US006932977B2

(12) United States Patent
Heidaran et al.

(10) Patent No.: US 6,932,977 B2
(45) Date of Patent: Aug. 23, 2005

(54) METHOD OF INDUCING OR ENHANCING CHONDROGENESIS WITH EXTRACELLULAR MATRIX CONTAINING BMP-4

(75) Inventors: Mohammad A. Heidaran, Los Gatos, CA (US); Robin Daverman, San Jose, CA (US)

(73) Assignee: Depuy Spine, Inc., Raynham, MA (US)

( * ) Notice: Subject to any disclaimer, the term of this patent is extended or adjusted under 35 U.S.C. 154(b) by 0 days.

(21) Appl. No.: 09/805,816

(22) Filed: Mar. 13, 2001

(65) Prior Publication Data

US 2002/0107205 A1 Aug. 8, 2002

Related U.S. Application Data

(60) Provisional application No. 60/197,235, filed on Apr. 14, 2000.

(51) Int. Cl.$^7$ .................................................. A61F 2/02
(52) U.S. Cl. ....................................................... 424/423
(58) Field of Search ................................ 424/422, 423, 424/424, 425, 484, 488, 426, 486; 514/2, 54; 523/114, 115; 423/423

(56) References Cited

U.S. PATENT DOCUMENTS

| 5,118,667 | A | | 6/1992 | Adams et al. ................. 514/12 |
| 5,902,785 | A | * | 5/1999 | Hattersley et al. .............. 514/2 |
| 6,309,670 | B1 | * | 10/2001 | Heidaran et al. ............ 424/486 |
| 6,514,514 | B1 | * | 2/2003 | Atkinson et al. ............ 424/423 |
| 6,586,406 | B2 | * | 7/2003 | Heidaran et al. .............. 514/21 |
| 6,699,471 | B2 | * | 3/2004 | Radice et al. ............... 424/93.7 |

\* cited by examiner

*Primary Examiner*—Carlos A. Azpuru
(74) *Attorney, Agent, or Firm*—Beyer Weaver & Thomas, LLP

(57) ABSTRACT

A method and composition are provided for inducing or enhancing chondrogenesis in vivo or in vitro. The method is performed by exposing the cells in vitro or in vivo to an extracellular matrix comprising of type I collagen, type II collagen or a mixture of type I collagen or type II collagen and hyaluronate and further containing BMP-4 or a combination of BMP-4 and GDF-5.

4 Claims, No Drawings

METHOD OF INDUCING OR ENHANCING CHONDROGENESIS WITH EXTRACELLULAR MATRIX CONTAINING BMP-4

This application claims priority from Provisional Application Ser. No. 60/197,235 filed Apr. 14, 2000.

BACKGROUND OF THE INVENTION

The limited capacity of articular cartilage to regenerate represents a major obstacle in the management of degenerative and traumatic joint injuries. The maintenance of a functional joint surface requires that articular chondrocytes respond to extracellular signals that are generated from growth and differentiation factors, mechanical stimuli, and interactions with specific components of the extracellular matrix. The invention is directed to an extracellular matrix of type I collagen, type II collagen, type I collagen plus hyaluronate, or type II collagen plus hyaluronate, and bone morphogenetic protein-4 (BMP-4). A combination of BMP-4 with differentiation factor-5 (GDF-5) is also useful.

Coordinated function of many cell types is regulated by integration of extracellular signal derived from soluble factors inducing growth factors and insoluble molecules such as extracellular matrix (ECM). The skeletal elements of the vertebrate limb are derived during embryonic development from mesenchymal cells, which condense and initiate a differentiation program that result in cartilage and bone. Bone morphogenetic proteins may play a crucial role in mesenchymal condensations in skeletal patterning, including the process of joint formation.

Despite the importance of joint formation in skeletal patterning and human disease, relatively little is known about the molecular mechanisms that control where and when a joint will form. In the limb, joints typically arise by the splitting of larger skeletal precursors, rather than by collision or apposition of separate elements. This process takes place through a series of steps including: 1) initial formation of specialized regions of high density that extend in transverse stripes across developing cartilage element; 2) programmed cell death and changes in matrix production in the center of the interzone, creating a three layer structure; 3) differentiation of articular cartilage at the two edges of the interzone; and 4) accumulation of fluid-filled spaces that coalesce to make a gap between opposing skeletal elements.

SUMMARY OF THE INVENTION

This invention is directed to a method and composition for inducing or enhancing chondrogenesis in cells with an extracellular matrix containing BMP-4 or a combination of BMP-4 and GDF-5. The extracellular matrix consists of type I collagen, type II collagen, type I collagen plus hyaluronate or type II collagen plus hyaluronate, and contains BMP-4 or BMP-4 and growth and differentiation factor-5, GDF-5. An effective amount of BMP-4 or combination BMP-4 and GDS-5 to induce or enhance chondrogenesis is about 1 ng to 10 mg/ml matrix protein. A matrix is a solid porous composition having a relatively fixed three-dimensional structure.

DESCRIPTION OF THE PREFERRED EMBODIMENTS

Chondrogenesis is induced by an extracellular matrix composition of type I collagen, type II collagen, type I collagen plus hyaluronate, or type II collagen plus hyaluronate containing BMP-4 or a combination of BMP4 and GDF-5. Type I and II collagen represent the most abundant ECM protein in bone and cartilage, respectively.

Collagen may be obtained from bone, tendons, skin, or the like. The collagen source may be any convenient animal source, mammalian or avian, including bovine, porcine, equine, or the like, or chicken, turkey or other domestic source of collagen.

Hyaluronic acid is a naturally-occuring polysaccharide containing alternating N~acetyl~D~glucosamine and D~glucuronic acid monosaccharide units linked with beta 1–4 bonds and disaccharide units linked with beta 1–3 glycoside bonds. It occurs usually as the sodium salt and has a molecular weight range of about 50,000 to $8 \times 10^6$.

The collagen or collagen-hyalurate mixture is provided as a matrix, typically by lyophilization. The collagen-hyaluronate is formed by treating collagen with an active formyl aldehyde hyaluronate, formed as described in U.S. Pat. No. 5,866,165, incorporated by reference herein. The collagen hyaluronate composition is also provided as a matrix by lyophilization.

The matrix is preferably implanted with an effective amount of BMP-4 or combination of BMP-4 and GDF-5, which is about 1 mg to 10 mg/ml of matrix protein.

To show in vitro application, fetal rabbit chondrocytes are plated on various purified extracellular matrix proteins in the presence of recombinant human BMP-4 or BMP-4 and GDF-5 (100 ng/ml) for 3 weeks and are scored for differentiation at the level of morphology, overall proteoglycan synthesis and deposition, and aggrecan and type II collagen expression. The BMP-4 and BMP-4 plus GDF-5 stimulate exponentially chondrogenic nodule formation of FRC's plated on type I or type II collagen. Chondrogenic nodules stained heavily with alcian blue and are positive for type II collagen and aggrecan-expression. Cells in monolayer that surround the nodules are negative for the chondrogenic markers.

Plastic plates are first coated with different ECM proteins including type I and II collagen, type IV collagen, or fibronectin. The BMP-4 and combination BMP-4 and GDF-5 stimulate the formation of chondrogenic cell aggregate that bind heavily to the alcian blue stain. Plastic culture 12 well (Costar, Cambridge, Mass.) are coated with 0.01% (w/v) of the indicated extracellular matrix proteins for 2 hours at 37° C. After removal of nonadsorbant protein, rabbit chondrocytes are plated at a density of $2 \times 10^5$ cells/well in DMEM containing 10% FBS. Culture plates are then maintained for 21 days in culture media supplemented with or without PMP-4 or BMP-4 plus GDF-5 (100 ng/ml). Plates are then stained overnight with alcian blue stain (0.5% w/v in 3% acetic acid), washed and photographed. For quantitation of alcian blue, cells are solubilized in 8M urea, and the amount of stain is quantitated using spectrophotometer (Molecular Devices, Sunnyvale, Calif.). Since alcian blue is a cationic dye which has been shown to bind to anionic proteins including proteoglycans.

To examine correlation of changes in cellular morphology with the process of chondrogenesis, total cellular RNA and protein are isolated from FRC culture treated with BMP-4 or BMP-4 plus GDF-5 in the presence of type I collagen. Total cellular RNA isolated from FRC cells is subjected to a semiquantitative PCR analysis using specific primers designed to amplify aggrecan, type II collagen or type I collagen. Expression of type II collagen and aggrecan mRNA is increased in cultures treated with BMP-4 or BMP-4 plus GDF-5.

Total cell lysates (100 ug) are electrophoretically separated on a 8% or 5% SDSPAGE, transferred to immobilon-P and immunoblotted using antibody specific to type II collagen or aggrecan. The BMP-4 or BMP-4 plus GDF-5 stimulate a significant increase in the steady state level of type II collagen and aggrecan.

The collagen is also provided in matrix form for in vivo use. Type I collagen fibers are dispersed at 2% weight % ratio in distilled water and homogenized 3 times for 5 seconds each at low speed in a heavy duty blender. The pH of the slurry is then adjusted to a) pH 3.0; b) pH 7 0; or c) pH 10.0 by adding HCl or NaOH as necessary. The slurry was then cast into molds and frozen at the following temperatures prior to lyophilization:

a) pH 3.0 slurry: −78° C., −40° C. or −20° C.

b) pH 7.0 slurry; −40° C.

c) ph 10.0 slurry; −40° C.

The lyophilization cycle for the above matrices are as follows: 0° C. for 2 hours; −40° C. for 2 hours; −20° C. for 2 hours; −4° C. for 4 hours; and 25° C. for 1 hour.

Hyaluronate containing active formyl aldehyde groups, prepared as disclosed in U.S. Pat. No. 5,866,165, are added to the above collagen matrices by immersion of the collagen matrix in a 2% weight % solution, pH 7–8 of the hyaluronate polyaldehyde. The immersed matrices are shaken at room temperature for 4 hours, washed 3 times and lyophilized using the lyophilization cycle described above for the collagen matrix preparation.

A porous matrix fabricated from type I collagen are seeded by, $1 \times 10^5$ cell per implant (2×3×3 mm). Cells embedded in matrices are then cultured for 3 weeks in culture supplemented with or without GDF-5 (100 ng/ml). Total RNA isolated from each implant are then subjected to RT-PCR. The BMP-4 and BMP-4 plus GDF-5 induce expression of aggrecan and type II collagen, two well known markers of chondrogenesis. In parallel the implant material is subject to histological evaluation followed by alcian or Toludine blue staining. The BMP-4 and BMP-4 plus GDF-5 are capable of inducing marked changes in cellular morphology of FRC underscored by increase in alcian blue staining and changes in cell shape. Under these conditions cells are not able to proliferate and differentiate in the ECM in the absence of BMP-4 or GDF-5 as measured by histological evaluation total DNA, RNA or protein content.

The cellular interaction with type I collagen significantly enhances the chondro-inductive activity of BMP-4 and BMP-4 plus GDF-5.

The BMP-4 and BMP-4 plus GDF-5 biological function is modulated by a type I collagen extracellular matrix composition and structure containing those factors. This event is regulated both temporally and spatially so one may use the matrix to regulate cellular morphogenesis and joint development in vivo.

The growth and differentiation factor-induced chondrogenesis is highly specific to BMP-4 and GDF-5. The ECM-dependent chondrogenesis by these factors is highly specific and can be shown by evaluating the ability of several mitogens and prototype differentiation factors under the following conditions. Chondrogenesis can be assessed by monochromatic staining of FRC cultured in the presence of type I collagen and various growth factors. For example, crude preparations of BMPs and TGFb, two other member of this class of differentiation factors, completely fail to stimulate chondrogenesis. In addition, growth factors including bFGF or IGF-I, IGF-II fail to stimulate chondrogenesis under these conditions.

What is claimed is:

1. A method for inducing chondrogenesis comprising the steps of contacting chondrocytes with a composition consisting of (a) an extracellular matrix formed by lyophilization of a dispersion comprising type I collagen fibers and (b) an effective amount of BMP-4 sufficient to induce chondrogenesis and culturing said chondrocytes in vitro with said composition.

2. A method for inducing chondrogenesis comprising the steps of contacting chondrocytes with a composition consisting of (a) an extracellular matrix formed by lyophilization of a dispersion comprising type II collagen fibers and (b) an effective amount of BMP-4 sufficient to induce chondrogenesis and culturing said chondrocytes in vitro with said composition.

3. A method according to claim 1 or 2 wherein said chondrocytes are from joint tissue.

4. A method according to claim 1 or 2 further comprising the step of subsequently implanting said matrix containing said chondrocytes into a site in vivo of desired chondrogenesis.

* * * * *